(12) United States Patent
Ford

(10) Patent No.: US 6,314,822 B1
(45) Date of Patent: Nov. 13, 2001

(54) PEAK FLOW METER

(76) Inventor: Thomas McDonald Ford, 2, Bridport Way CM 7 9FJ, Braintree (GB)

(*) Notice: Subject to any disclaimer, the term of this patent is extended or adjusted under 35 U.S.C. 154(b) by 0 days.

(21) Appl. No.: 09/268,005

(22) Filed: Mar. 15, 1999

Related U.S. Application Data

(6362) Continuation-in-part of application No. 08/849,647, filed as application No.PCT/GB95/02793 on Nov. 29, 1995, now abandoned.

(30) Foreign Application Priority Data

Nov. 30, 1994 (GB) .................................................. 9424230

(51) Int. Cl.[7] .............................. G01F 15/00; G01F 1/28
(52) U.S. Cl. .................................... 73/861.77; 73/861.74
(58) Field of Search ........................... 73/861.74, 861.75, 73/861.77, 861.79

(56) References Cited

U.S. PATENT DOCUMENTS

| 4,292,853 | * | 10/1981 | Williams et al. | ................. | 73/861.79 |
| 4,294,262 | * | 10/1981 | Williams et al. | ................. | 73/861.77 |
| 5,469,750 | * | 11/1995 | Lloyd et al. | ........................ | 73/861.61 |
| 5,638,174 | * | 6/1997 | Henderson | ......................... | 73/861.77 |

* cited by examiner

Primary Examiner—Harshad Patel
(74) Attorney, Agent, or Firm—Orum & Roth

(57) ABSTRACT

An air-flow measuring device for measuring respiratory performance includes a valve having at least one rotary blade for detecting air-flow through the device. The valve includes at least one air-directing aperture which alters the direction of air-flow incident on said valve from a first direction onto a second altered direction. The second direction is perpendicular to the first direction and to the planar surface of the rotary blade. The direction-altered air-flow provides a force which causes the rotary blade to move. An optical transducer measures the rotation of the blade to determine air-flow parameters in the device.

13 Claims, 8 Drawing Sheets

PEAK FLOW METER

The present invention is a Continuation-in-Part application of Ser. No. 08/849,647 filed on May 29, 1997 (now abandoned) based on International (PCT) Patent Application No. PCT/GB95/02793, filed Nov. 29, 1995.

FIELD OF THE INVENTION

This invention relates to the field of apparatus for measuring lung function. Particularly, the present invention relates to an air-flow valve for measuring the volume of air which can be expelled from the lungs and to a device incorporating such a valve to give improved indication of lung function.

BACKGROUND TO THE INVENTION

During normal adult respiration, the amount of air inspired or expired per breath (tidal air) is approximately 500 ml.

After a normal tidal expiration, a further volume of air (the expiratory reserve-volume) can be expired—approximately 750–1000 ml in adults.

Vital capacity is the maximum volume of air which can be expelled from the lungs by a forceful effort, following a deliberate inhalation of the maximum volume possible. This vital capacity is normally of the order of 4.8 liters in men and 3.2 liters in women, but can be substantially reduced in asthmatics and people with other bronchial problems. The vital capacity and/or the ability to exhale thus provides a good indication of a subject's function.

Several devices exist which monitor a subject's ability to exhale, thus providing an indication of lung function. These devices employ a number of different methods which either directly or indirectly provide a measurement of expiratory volume; tidal reserve or more preferably vital capacity. For example, a subject may be asked to blow into a calibrated tube containing a spring-loaded device, such as a piston, which is moved along a calibrated scale according to the force provided by the exhaled air. The inertia of the spring-loaded device will affect the sensitivity of the equipment and may require that, for a valid measurement, a degree of force is needed which a severe asthmatic, or an otherwise respiratory-impaired individual, cannot provide.

An alternative method involves the use of a device containing a hot wire. Exhaled air passes over the hot wire, cooling it and a measure of the degree of cooling thus provides an indication of lung function. Again the device may not be sensitive enough for some objects. In addition the difficulty in accurately measuring the degree of cooling further affects the sensitivity.

A further method involves the use of rotary blades or a turbine. Exhaled air causes the blades to rotate and this motion is detected and translated into an indication of lung function. Turbines generally are heavy for their size and do not provide the required sensitivity. Rotary blade devices are generally arranged so that the exhaled air impinges on the edges of the blades (i.e. that is, perpendicular to their mountings) and, again, the inertia of the device will affect its sensitivity. This is particularly important for testing subjects with poor lung function.

Breath volumeters of this type are exemplified by the disclosure of German Patent Specification No. DE-A-1803325 (VEB MEDIZINTECHNIK LEIPZIZ) which describes a breath volumeter having a rotor fitted with a twin-armed vane arranged centrally below a semi-circularly shaped stator attached to the meter casing. The stator has a roughly semi-cross-section. In use, this arrangement suffers the disadvantage of developing a significant back-pressure in the device which is undesirable as it adversely affects the sensitivity and efficiency of the device.

The provision of back-pressure in such a device is essential if the parameter known as Force Expired Volume (FEV1) to be measured. This parameter, which is a measure of expired volume per second after initial exhilation and gives an indication of vital lung capacity and tidal reserve, is particularly important for assessing bronchitis and similar conditions. If back-pressure in a device is too low, a poor indication of vital capacity is received. Conversely, if back-pressure is too high, subjects having poor lung function will be unable to provide sufficient force to operate the device. Sensitivity of the device will also be adversely affected.

In all such breath volumeters, the inertia of the rotating blades or turbines is critical. High inertia results in slow acceleration of the blades and a continuation of rotation after the applied exhilation ceases will result. One problem associated with prior art devices is the exposure of the blades to moisture or sputum carried on the exhaled breath. A build-up of such deposits on the blade will naturally affect its inertia and consequently, the accuracy of the device. Devices where the breath is applied directly to the blades or where the air-flow is re-directed marginally to impinge the blades are particularly vulnerable. Where optical means are provided to measure device parameters, the deposits mentioned above also have a deleterious affect. Thus. Peak Flow readings, which are of particular interest for analysing asthma sufferers, may be affected.

U.S. Pat. No. 4,292,853, issued Oct. 6, 1981 to Williams et al discloses a respiratory air or gas flow volume indicating instrument having a slotted stator for directing exhaled air onto a rotor. By means of a barrier and a shaped gallery about the stator, air is constrained to flow in one direction about the stator, through the stator slots onto the blades or vanes of the rotor. The rotor spindle, to which the vanes are axially fixed, drives a pointer through a counting gear box to indicate the volume of air flow.

The U.S. Pat. No. 4,292,853 arrangement possesses the disadvantageous features referred to above. Firstly, the inertia of the rotor which is connected to a gearbox limits the allowable sensitivity and could not be used for accurate peak flow measurement. Secondly, air flow from the inlet can directly impinge the rotor allowing food particles, sputum or excessive vapour to adhere thereto. Additionally, the construction disclosed does not allow for easy disassembly and cleaning. Further, mechanical coupling of the rotor to a counting mechanism allows only for measurement of one parameter, in this case, volume flow. Finally, as the flow of air is constrained in the gallery, back pressure is relatively high (although stated to be tolerable) even though the flow path is relatively simple. The air flow path described is an inlet air flow perpendicular to the rotational axis of the rotor and an angular deflection into the gallery before being directed spirally inwards to impinge the rotor vanes.

U.S. Pat. No. 4,294,262, issued Oct. 13, 1981 to Williams et al describes a respirometer having a circular chamber having a rotor therein. The arrangement disclosed is essentially that forming part of U.S. Pat. No. 4,292,853 but having magnets mounted on radial arms rotatable with the rotor spindle. The magnets co-operate with at least one magnetic field sensitive device arranged to sense the rotation of the rotor. An electrical output is then available for manipulation to obtain the required respiratory parameters.

In addition to the disadvantages ascribed to the U.S. Pat. No. 4,292,853 arrangement, the affect of the magnets mounted on the radial arms is to increase the mass of the rotor, thus increasing inertia and decreasing sensitivity.

It will be appreciated that none of the prior art devices lend themselves to repeated cleaning or sterilisation.

It is an object of the present invention to overcome the disadvantages described above and to provide an apparatus for measuring respiratory performance which is more sensitive than prior art devices.

It is a further object of the invention to provide an improved an air-flow valve for use in a device for measuring respiratory function.

It is a yet further object of the invention to provide an air-flow measuring device which is easily cleaned or sterilised.

SUMMARY OF THE INVENTION

In its broadest aspect, the invention concerns the advantageous manipulation or redirection of an air-flow in an apparatus for measuring respiratory function.

According to a first aspect of the present invention there is provided an air-flow valve for use in a device for measuring air-flow, said valve including at least one rotary blade means comprising a planar surface free along at least one edge, for detecting air-flow thereabout, and a stator having at least one air-directing aperture positioned at, or adjacent, the outer edge of said blade means or the outermost part of the path traced by the same, said aperture being adapted to alter the direction of air-flow incident on said valve from a first direction to a second altered direction, whereby said direction-altered air-flow provides a force which causes said blade means to move, said first direction being substantially parallel to the rotational axis of said blade means and said direction being tangential to the rotational axis of said blade means and said second altered direction being perpendicular to or at least towards the planar surface of said blade means.

It will be seen that by applying an air-flow which is changed from a direction parallel to the rotational axis of the blade, firstly to a direction where the major force component is perpendicular to said axis but in the opposite sense and subsequently reversing the sense (to build back-pressure), before finally being angularly deflected to impinge on the blades, facilitates the use of blade means having low inertial properties. The use of such a blade means allows for an extremely sensitive air-flow valve to be realised.

The air-directing apertures or slits are profiled angularly deflect the air-flow to direct it to or towards the planar surface of the blade so causing the blade to turn.

Conveniently, a valve body for housing the stator and rotor is provided, at least part of said valve body, in the region of said blade means, being transparent or translucent. This is favoured because a motion detecting means which relies on the transmission and detection of an infra-red or light beam can be used with the valve. Preferably, apertures are provided in the valved body to allow the passage of either an infra-red or light beam therethrough.

Conveniently, the blade means rotates through a predetermined sector, which sector includes the path of the infra-red or light beam, interruptible by the passage of the blade means therethrough.

Air-directing means are associated with each of the air-directing apertures to guide air from an annular chamber around the stator through the apertures onto the planar surface of the blade. The apertures which are equi-spaced about the stator are shaped as air-directing means as the apertures are profiled to angularly deflect air into a direction tangential to the rotor axis.

In one arrangement, the stator includes a plurality of fins positioned around the stator substantially adjacent each of said air-directing apertures.

In a further arrangement, the air-directing means comprises a plurality of air-flow guides positioned substantially adjacent each of said air-directing apertures, the air-flow guides being adapted to facilitate the change in air-flow direction from said first direction to said second direction.

Conveniently, said plurality of air-flow guides are formed as a valve insert adapted to cooperate with the stator, said guides being positioned to correspond to the air-directing apertures of the stator.

The air-flow valve of the invention is ideally suited for use in an air-flow measuring device, and preferably includes mans for releasably securing the valve to such a device. The valve is made from a number of easily assembled and disassembled components thus facilitating cleaning. The valve components preferably comprise plastics material or other suitable material to withstand regular sterilisation.

According to a second aspect of the present invention, there is therefore provided a device for measuring air-flow comprising:

an air inlet;

an air-flow valve, substantially as defined above, including at least one blade means adapted to rotate in response to a force directed through the air inlet;

one or more optical transducers adapted to monitor the movement of said blade means;

processing means for determining a required parameter from the output(s) of said optical transducer(s); and display means for visually representing said required parameter.

Preferably, the blade means is arranged to affect said optical transducers so as to interfere with or interrupt either an infra-red or a light beam.

Conveniently, said valve body includes a mouthpiece which is releasably connected to the valve body so that a variety of mouthpieces can be attached to the device.

Advantageously, the valve is releasably attached to the device to facilitate cleaning or substitution of the valve.

BRIEF DESCRIPTION OF THE DRAWINGS

The present invention will now be described more particular with reference to the accompanying drawings which show by way of example only, one embodiment of air-flow valve for use with a device for measuring air-flow and four stator arrangements for use with the air-flow valve. In the drawings:

FIGS. 5D and 5E show a top plan view and a bottom plan view of the valve body of FIG. 5a;

DESCRIPTION OF THE EMBODIMENT

Figure 1A:
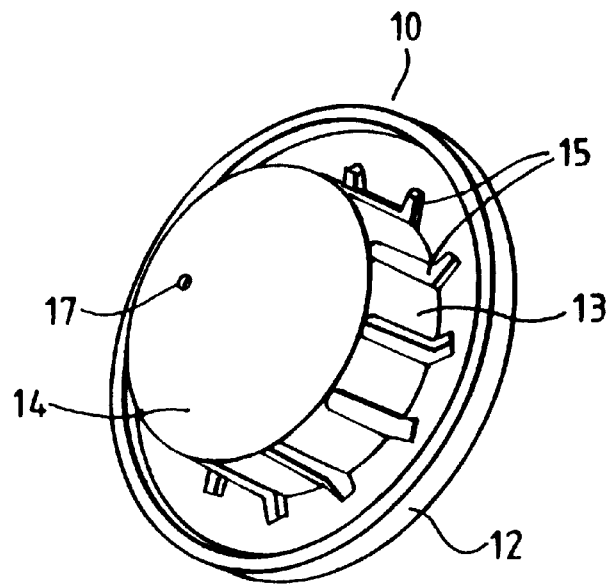
FIG. 1A shows a top perspective view of a first arrangement of air-directing stator according to the present invention.
Figure 1B:
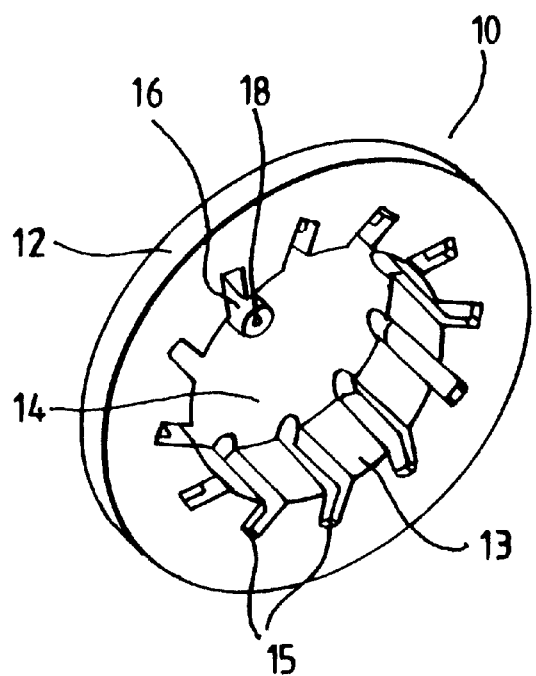
FIG. 1B shows a bottom perspective view of the stator of FIG. 1A.

Referring to the drawings and initially to FIGS. 1A and 1B, the air-flow valve of the invention comprises a first arrangement of stator 10 consisting of a hat-shaped body having a rim 12, a riser 13 and an upper region 14 which is conical.

Air-directing apertures 15 are provided in the riser 13. A rotor bearing 16 is provided at the apex of the conical upper region 14 and comprises a screw adjuster 17 and spindle seat 18.

Figure 2A:
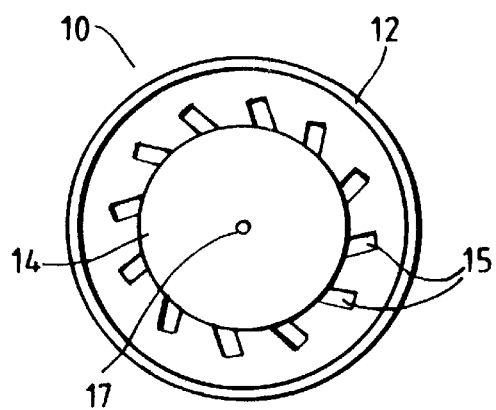
FIGS. 2A and 2B show a top plan view and a bottom plan view of the first arrangement of air-directing stator, respectively.
Figure 2B:
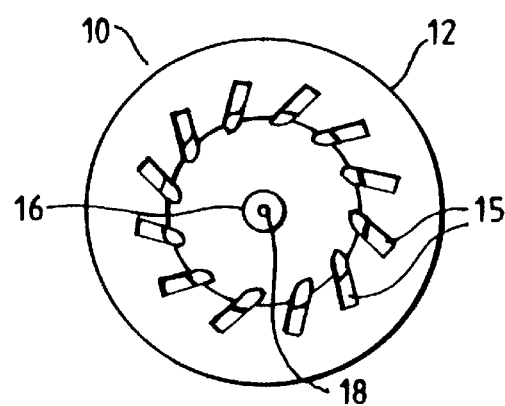

FIGS. 1A, 1B, 2A and 2B show more particularly the positioning of the apertures 15 in the first arrangement of stator 10, the apertures 15 being equi-spaced around the periphery of the riser 13. The apertures 15 extend the height of the riser 13 and extend also towards the rim 12, as shown in FIGS. 2A and 2B. The apertures 15 are angled axially so as to efficiently direct air-flow. Alternative forms of stator, for example, where the apertures extend towards the rim by means of upstanding fins or flaps (FIGS. 11 and 12), will be described hereinafter.

Figure 3A:
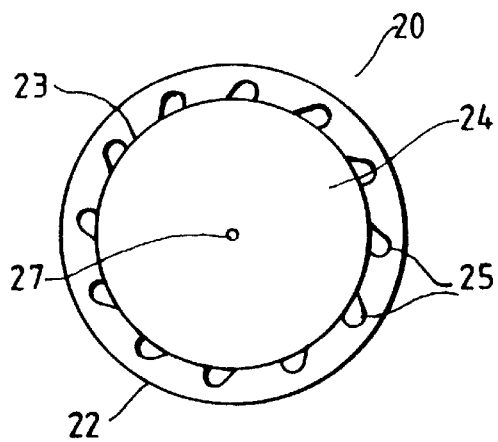
FIGS. 3A and 3B show a top plan view and a bottom plan view of a second arrangement of air-directing stator, respectively.
Figure 3B:
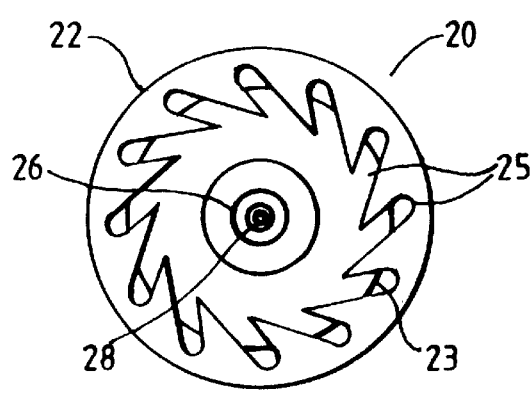

A second arrangement of stator 20, as illustrated in FIGS. 3A and 3B, has a hat-shaped body similar to that of the first stator 10. The stator 20 has a flattened rim 22, a riser 23 and conical upper region 24, as before. The radial position of the riser 23 is relatively closer to the rim 22 and the conical upper region 24 accordingly has a shallower gradient. Air-directing apertures 25 are provided about the periphery of the riser 23 and the apertures extend axially inwards to a greater extent than the apertures 15 illustrated with respect to the first arrangement of stator 10.

Figure 4A:
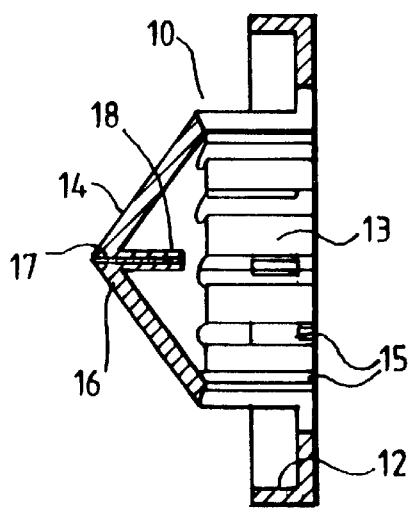
FIG. 4A shows a sectional side view of the second arrangement of air-directing stator.
Figure 4B:
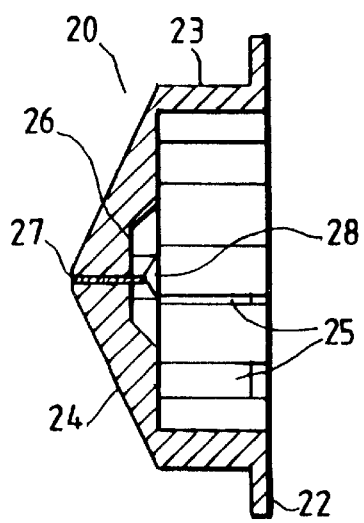
FIG. 4B shows a sectional side view of the second arrangement of air-directing stator.

FIGS. 4A and 4B show in cross-section the first and second arrangements of stator 10, 20, respectively, and illustrate the provision of the rotor bearing 16, 26 depending along the central axis of the stator 10, 20 from the apex of the conical region 14, 24.

Figure 5A:
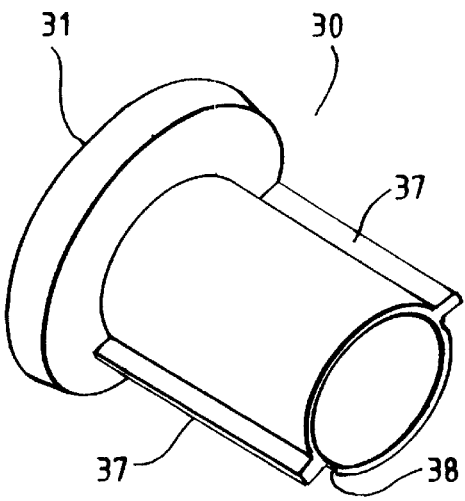
FIGS. 5A, 5B and 5C show a first bottom perspective view, a second bottom perspective view and a top perspective view of a valve body, respectively.
Figure 5B:
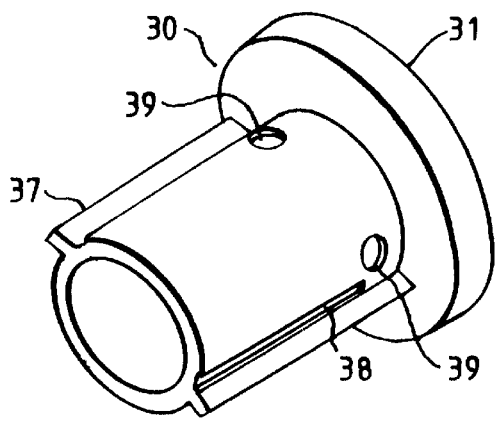
Figure 5D:
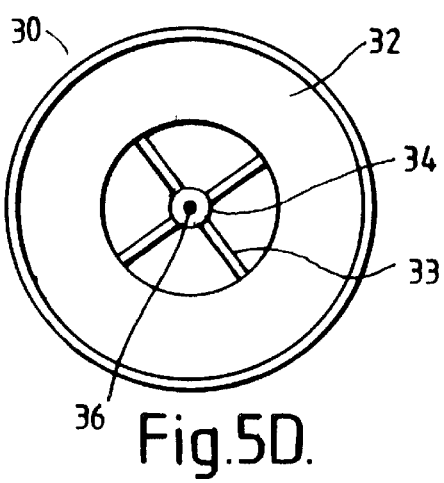
Figure 5C:
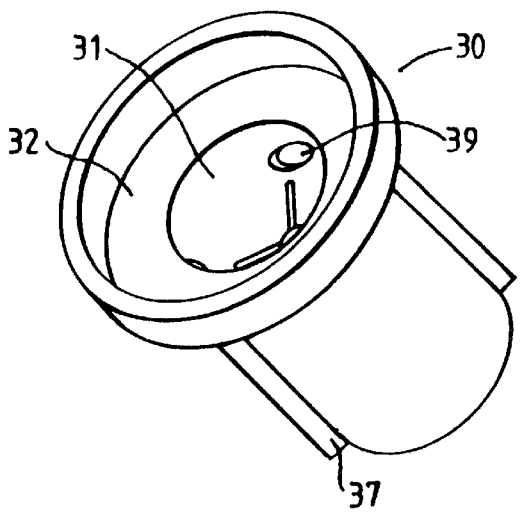
Figure 5E:
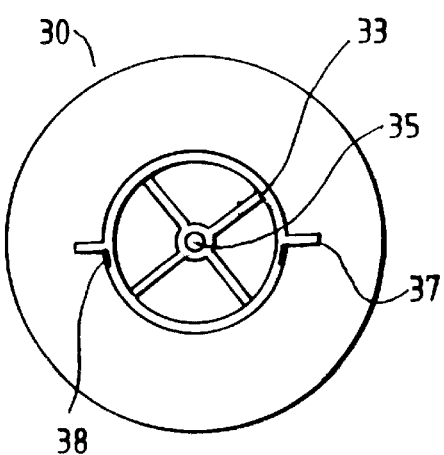
Figure 5F:
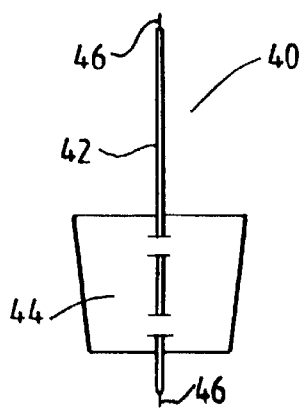
FIG. 5F shows a rotor mountable in the valve body and held therein by a stator.

Referring now to FIGS. 5A to 5F, the air-flow valve further comprises a substantially tubular body 30 having an open mouth 31, including a land 32, in which the stator 10, 20 sits. A cross member 33 is provided within the body for fixing a second rotor bearing 34, again comprising a screw adjuster 35 and a spindle seat 36. When the stator 10, 20 is in place, a rotor 40 is held between the stator mounted bearing 16, 26 and the second bearing 34. The bearings abut opposite ends of a spindle 42 on which a blade or blades 44 are mounted, as illustrated in FIG. 5F. To complete the air-flow valve, a mouthpiece 50 (as shown in detail in FIGS. 6A to 6C) is provided which sits into the valve body 30 by way of a push fit connection. The valve is adapted to be removable from an air-flow measurement device and to facilitate this the valve body 30 is provided with a pair of positioning flanges 37 extending radially therefrom and includes detent grooves 38 for co-operating with a fixing bead to allow snap fitting of the valve to a measuring device. A pair of apertures 39 is provided in the valve body 30 to allow optical detection of the rotation of the rotor 40.

In the preferred construction, the rotor 40 comprises a metal spindle 42 having tapered ends 46 (for low function interaction with the bearings) and a unitary rotor blade 44 which is glued, threaded or otherwise fixed to the spindle. The preferred blade material is a thin sheet of rigid plastics material such as celluloid or the like. The low inertia of this construction allows the rotor 40 to be accelerated from zero to approximately 80,000 r.p.m in milliseconds and facilitates extremely sensitive and accurate air-flow measurements.

In an alternative construction, the rotor blade 44 can be integrally formed with its shaft 42 and can have self-lubricating bearings. The blade 44 can be any convenient shape but the preferred shape is substantially rectangular. The position of the rotor blade 44 is such that when the assembled valve is attached to a measuring device of the type described below, the blade 44 is located between an infra-red or light beam emitter and its corresponding detector.

Figure 6A:
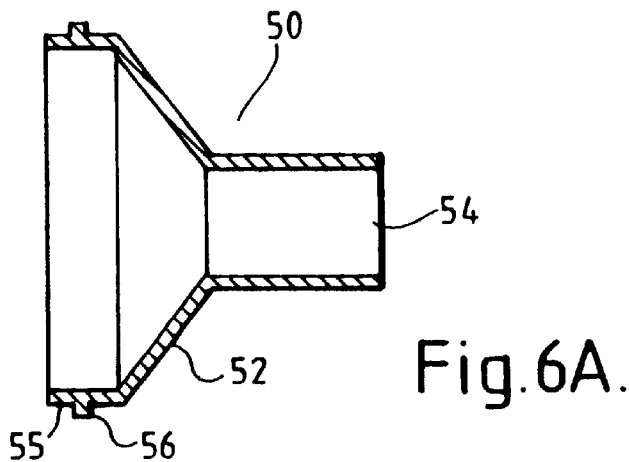
FIG. 6A shows a sectional view of a mouthpiece for attachment to the valve housing.
Figure 6B:
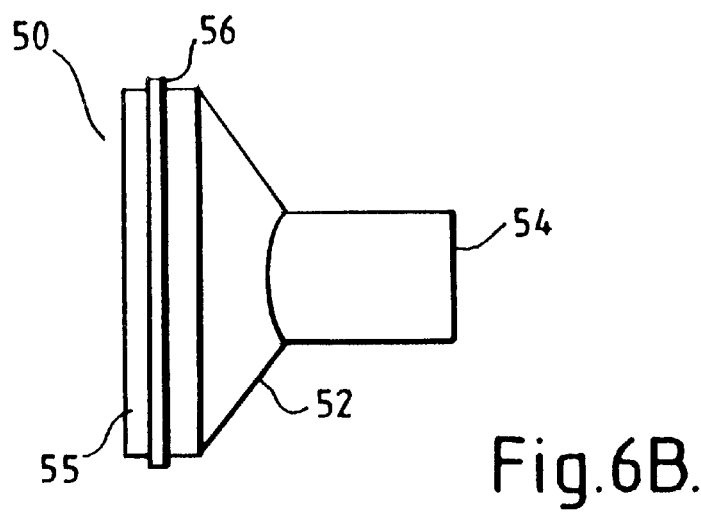
FIG. 6B shows a side view of the mouthpiece.
Figure 6C:
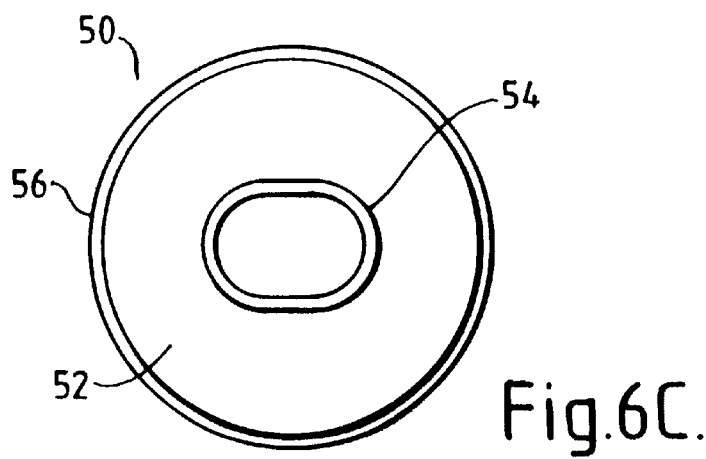
FIG. 6C shows a top plan view of the mouthpiece of FIG. 6A.

As illustrated in FIGS. 6A to 6C, the mouthpiece 50 consists of a conical or funnel-shaped portion 52, shaped to correspond with the conical upper region 14, 24 of a stator 10, 20, and has integrally formed therewith an air inlet 54 about which a test subject or patient places their lips to exhale air into the air-flow valve. The inlet 54 may have an ovoid cross-sectional shape but a proportionally larger, circular aperture is preferred for use with weaker test subjects. At the other end of the mouthpiece 50, a rim 55 is provided to engage the open mouth 31 of the valve body 30. An annular flange 56 is positioned adjacent the rim 55 to facilitate a sealing engagement of the mouthpiece 50 to the valve body 30. The distance between the flange 56 and the rim edge is selected with respect to the type of stator 10, 20 used.

In the following drawings, the first arrangement of stator 10 is shown and the rim 55 of the mouthpiece 50 abuts against the stator rim 12. However, it will be appreciated that if the mouthpiece rim 55 is extended, the corresponding height of the stator rim 12 can be reduced or eliminated altogether (as in the second stator arrangement).

As stated above, the air-flow valve is constructed to be detachable from an air-flow measuring device, thus facilitating replacement or interchanging of an air-flow valve from an air-flow measuring device. Further, the air-flow valve is made of material which can be easily sterilised without damage and may be disassembled for thorough cleaning.

To assemble the valve, the stator 10, 20 is inverted and one tapered end 46 of the rotor spindle 42 is positioned in the bearing seat 17, 27. The valve body 30 is then positioned over the stator 10, 20 and the free end of the spindle 42 is guided into the corresponding bearing seat 36 mounted in the cross member 33 of the valve body 30. The mouthpiece 50 is then placed over the conical region 14, 24 of the stator 10, 20 to secure the valve components in fixed relationship to one another. Adjustments to the rotor bearings 16, 26, 34 are then made to ensure minimal rotational friction on the rotor 40.

Figure 7:
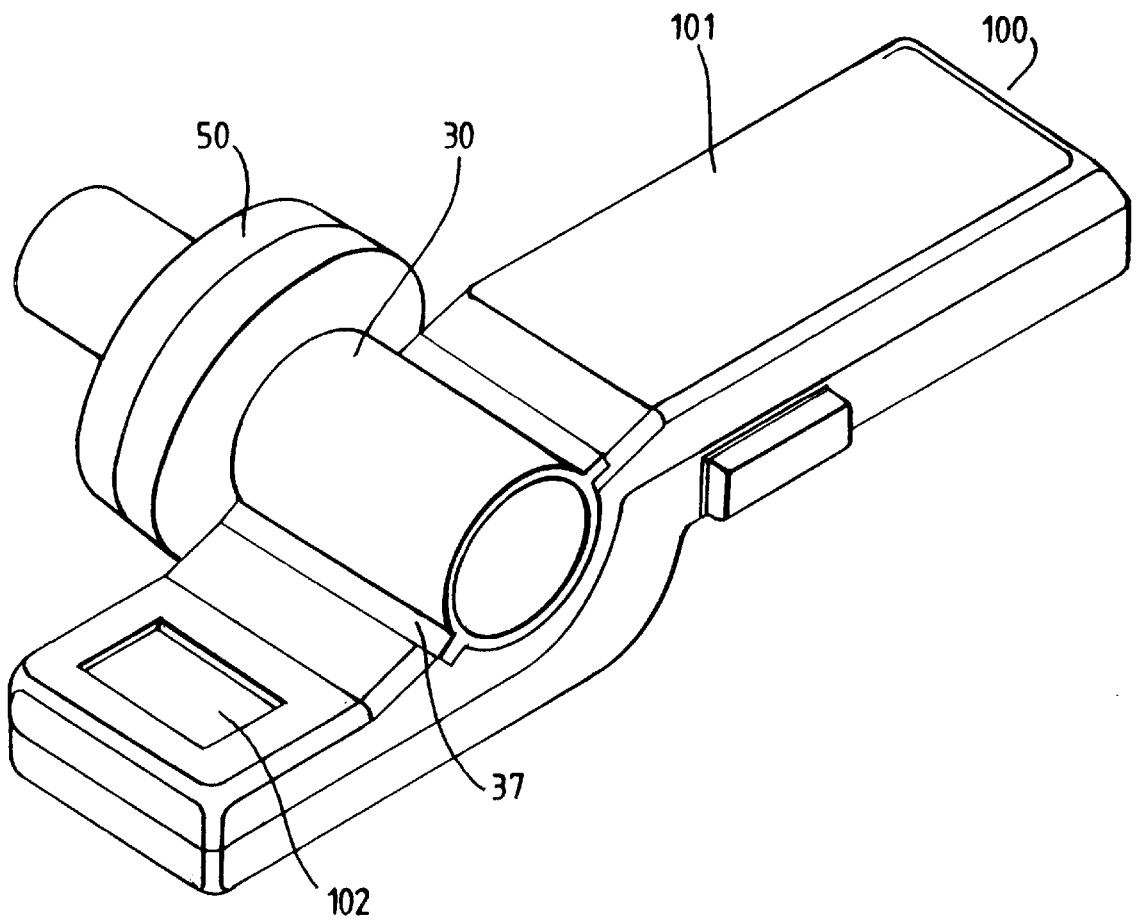
FIG. 7 shows a perspective view of a device for measuring air-flow.
Figure 8:
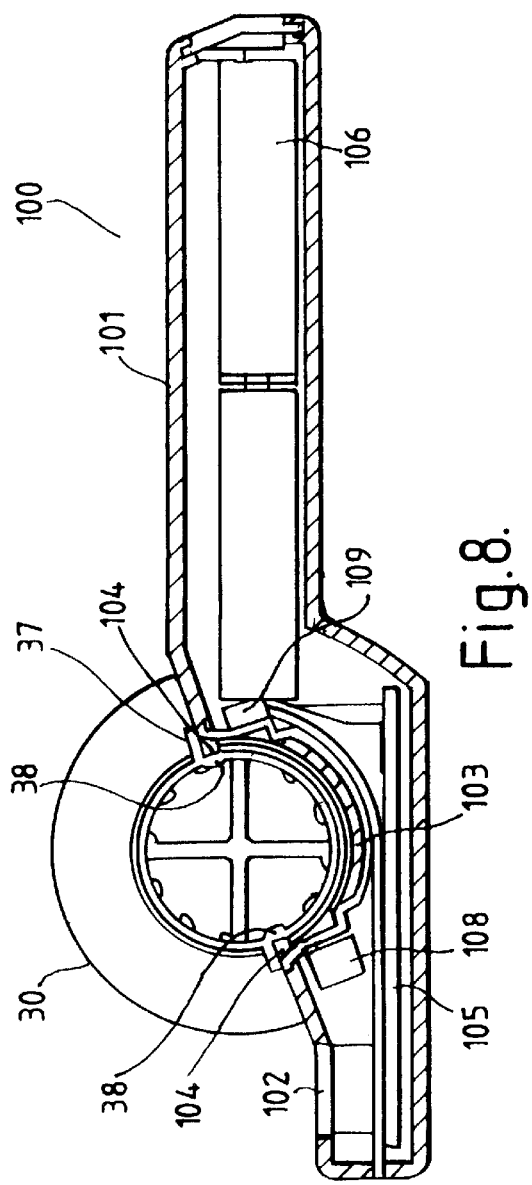
FIG. 8 shows a sectional side view of the device of FIG. 7.
Figure 9:
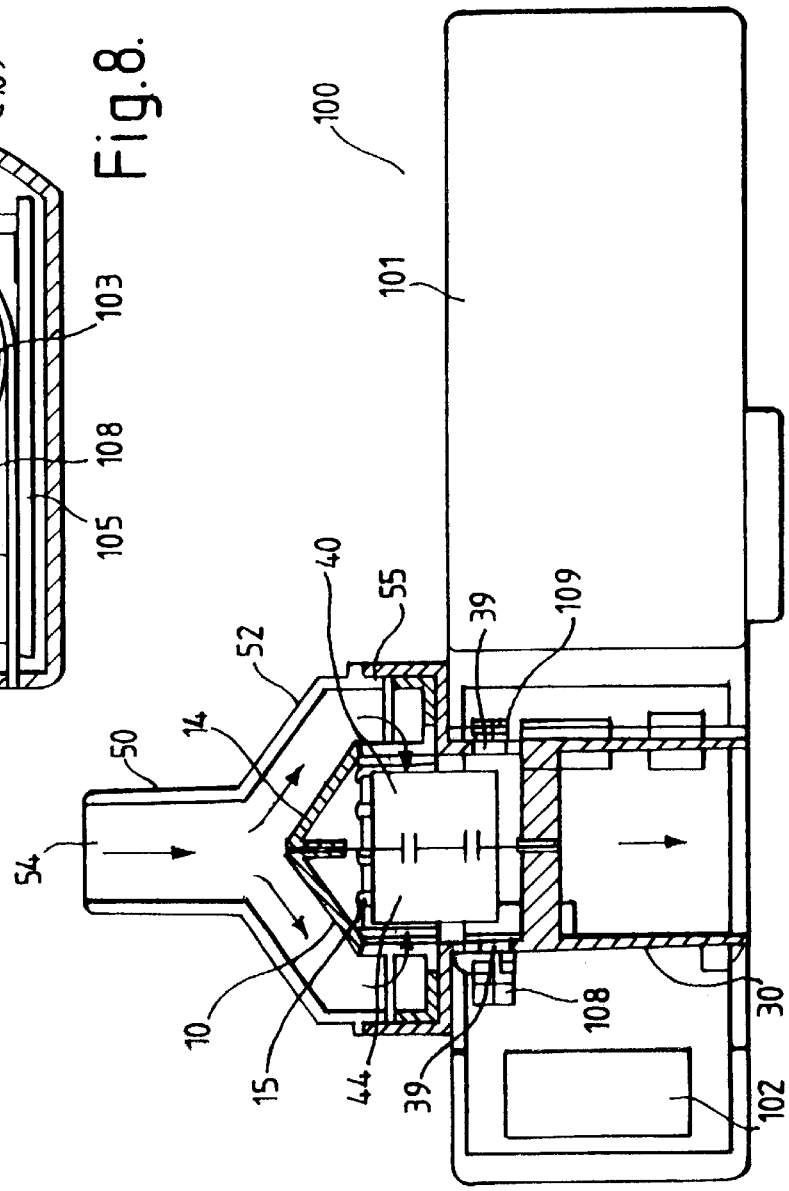
FIG. 9 shows a top view of the device partly in cross-section.

FIGS. 7, 8 and 9 show an assembled apparatus for measuring respiratory performance. The assembly comprises an air-flow valve, as hereinabove described, and a device 100 having a housing which is profiled to be a hand-held instrument to which the valve is releasably attached. The housing includes a battery compartment 101, a display 102 and a semi-circular recess 103 which includes a pair of securing beads 104 for engaging the corresponding detent grooves 28 in the valve body 30. The grooves 38 and beads 104 together with the positioning flanges 37, which abut the housing, position the valve into the semi-circular recess 103. This positively locates the valve body apertures 39 across an infra-red or light beam generated by the device 100.

The device 100 is provided with a printed circuit board 105 which is powered from batteries 106 in the battery compartment 101 and generates an infra-red or light beam between optically-coupled semi-conductor elements 108, 109 positioned so as to transmit and receive the beam through the apertures 39 provided in the valve body 30. Data processed by the circuit board 105 is presented on the display 102.

In use, a test subject blows or exhales into the mouthpiece 50, the exhaled air is directed as indicated by the arrows in FIG. 9. The rotor 40 rotates under the influence of the directed air and interrupts the infra-red or light beam as it rotates. The number of interruptions to the beam is indicative of the speed of the rotor 40. The volume of air expelled by the subject is a function of the rotor speed and the duration for which the rotor is moving. The circuitry mounted on the circuit board 105 measures the speed of the rotor 40 to calculate air-flow parameters as required. As the exhaled air enters the air inlet 54, it impinges the conical upper surface 14, 24 of the stator 10, 20 and is spread outwardly over that surface 14, 24 as constrained by the corresponding inner profile 52 of the mouthpiece 50. A back-pressure develops as the exhaled air accumulates in a chamber defined between the stator 10, 20 and the valve body 30 or mouthpiece rim 55. To escape, the air must substantially change direction from that imposed by the mouthpiece 50 and stator 10, 20 constriction. The air flows through apertures or slits 15, 25 and is angularly deflected by the aperture profiles into a direction which is towards or perpendicular to the planar surface of the blade 44.

Figure 10:
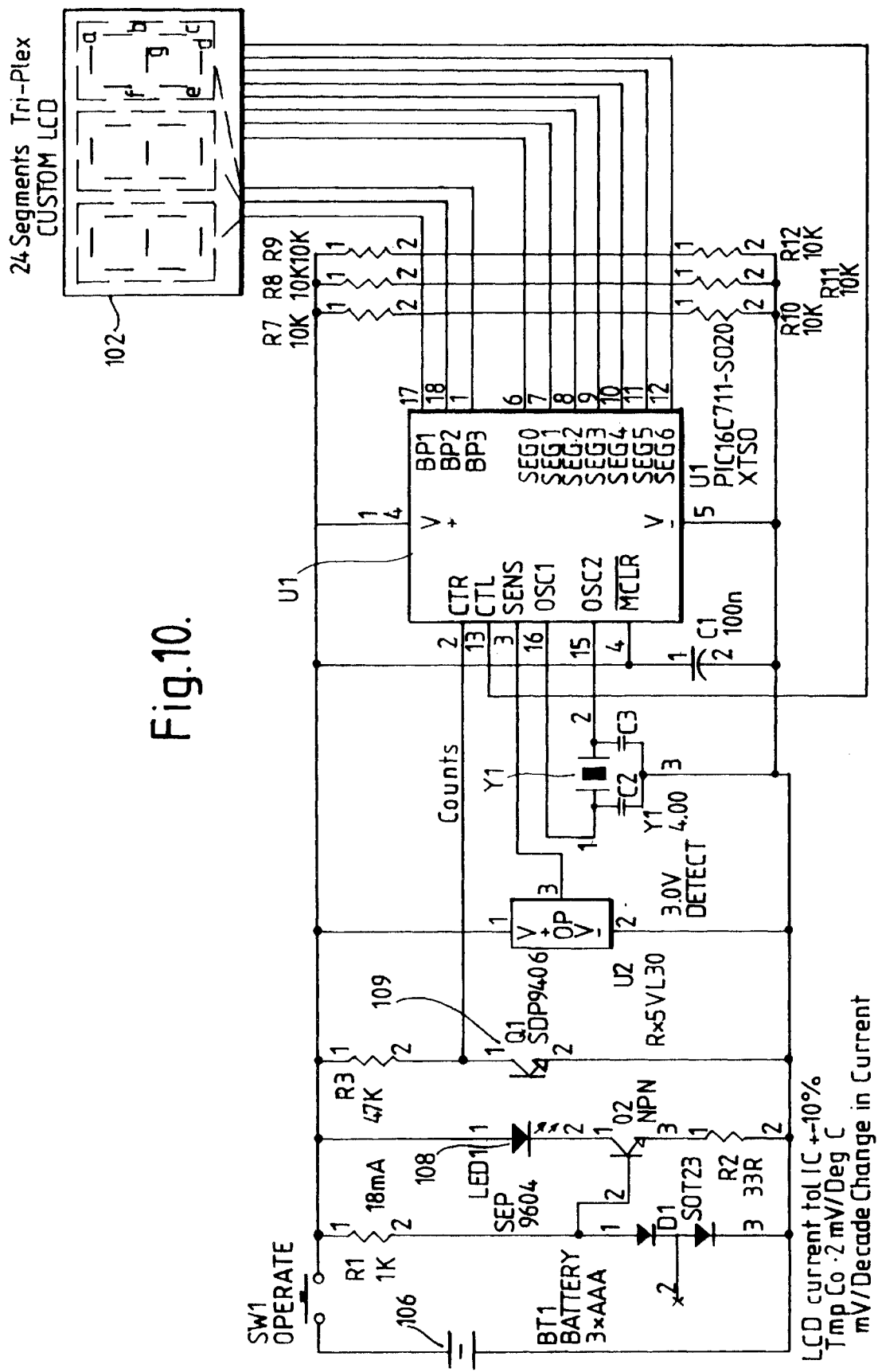
FIG. 10 is a schematic circuit digram of optical, processing and displaying elements of the device.

Referring now to FIG. 10, the electronic circuitry for use in the measuring device is shown schematically. Power is provided from batteries via a push button switch which initially resets a microcontroller U1 (PIC 16C 11SO20) and enables a counter. Infra-red or visible light is emitted by a light emitting diode 108 (LED1) and is received by an optical sensor element 109 (Q1). Interruptions to the light beam cause a pulse to be sent to the micro controller U1 which counts the pulses. The pulse count is compared against time, as measured using an oscillator which is controlled by a crystal Y1. The air-flow parameters required for presentation on a liquid crystal display (LCD) 102 are pre-programmed into the micro controller U1. By obtaining a measure of the fastest pulse count period, the peak flow of air exhaled by a subject is obtained. Similarly, by counting the number of pulses over a given period, for example, 0.5 seconds after peak flow is recorded, the FEV1 measurement is made. The FEV1 value and peak flow measurement are then displayed on the LCD 102. Preferably, the measurements are flashed on the LCD 102 alternately and for a period after the operating switch has been released. This allows a physician or tester adequate time to record the measurements. Appendix 1 attached herewith, provides a list of component values and further details of the components used in the circuit.

Figure 11:
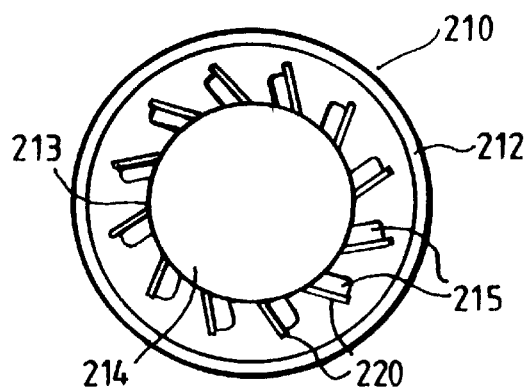
FIG. 11 is a top plan view of a third arrangement of stator having air-directing fins.
Figure 12:
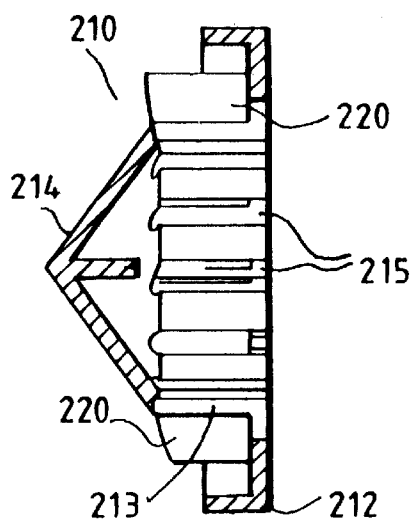
FIG. 12 is a side sectional view of the stator of FIG. 11.

A third arrangement of stator 210 as shown in FIGS. 11 and 12, comprises a hat-shaped body having a rim 212, riser 213 and an upper conical region 214, substantially identical to the first stator arrangement 10. Air-directing apertures 215 are provided as before, however, each aperture 215 is flanked by a fin 220 extending from the aperture towards to the rim 212. The fins 220 are preferably integrally formed with the stator 210 but may be glued or otherwise fixed to the riser 213 or apertures 215. The fins 220 may extend fully to the rim 212.

Where a mouthpiece 50 having an air inlet 54 of a relatively large diameter is recommended, the use of a stator without fins 220 is preferred to compensate for the resultant change in back-pressure.

Figure 13:
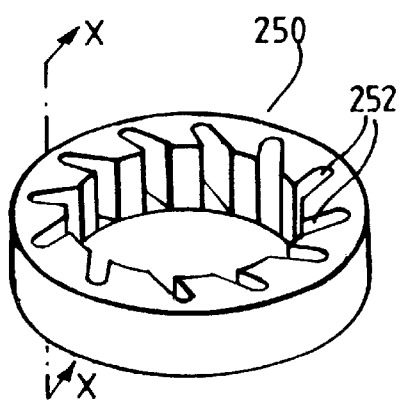
FIG. 13 is a perspective view of a valve insert.
Figure 14:
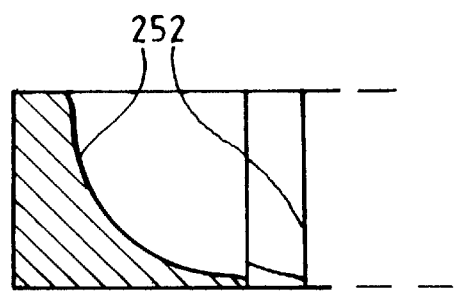
FIG. 14 is a cross-sectional elevation of the insert taken along lines X—X of FIG. 13.

The air-flow valve can include a fourth arrangement of stator comprising two parts. The first part comprises a stator similar or identical to the first or second stator arrangements 10, 20. The second part, as illustrated in FIGS. 13 and 14, comprises a valve insert 250 which, in use, is placed over the stator 10, 20 and fits into the chamber defined between the stator 10, 20 and the valve body 30 or mouthpiece 50. The insert 250 comprises essentially a ring having a series of air-flow guides 252 arranged to correspond with the apertures 15, 25 in the riser 13, 23 of the stator 10, 20. These guides 252 act to assist the smooth transition in direction of the air-flow from the air-inlet 54 towards to the rotor blades 44. The guides 252 have a curved shape, shown in detail in FIG. 14, which cause incident air to sharply but smoothly change direction. Back-pressure in this arrangement is less than that encountered with the stators 10, 20, 210 alone. This arrangement of air-flow valve, that is, with the insert 250 in place, is particularly effective for testing subjects where the incident air-flow rate is anticipated to be low.

Figure 15:
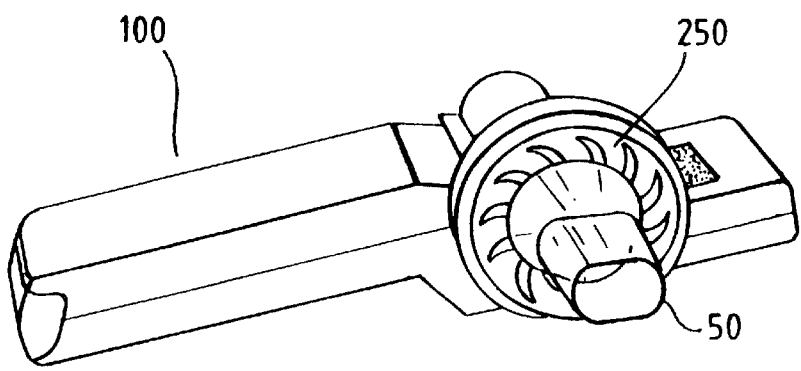
FIG. 15 is a side perspective view of an air-flow meter having a transparent mouthpiece and incorporating the insert of FIG. 13.

FIG. 15 is a perspective view of an apparatus for measuring respiratory function 100 having a transparent mouthpiece 50 (for clarity) and incorporates an insert 250 of the type described above.

The air-flow valve of the invention thus provides a means of increasing the sensitivity of an apparatus for measuring respiratory performance by simply making maximum use of expired air. Re-direction of air-flow is employed in this way in order to reduce inefficiency of existing systems.

It will of course be understood that the invention is not limited to the specific details described herein, which are given by way of example only, and that various modifications and alterations are possible within the scope of the amended claims.

APPENDIX 1

Typical values are given, exact values will depend upon the particular selection of microcontroller, crystal and optical components.

| R1 | 1K | 5% tolerance |
|---|---|---|
| R2 | 33K | 5%, exact value will depend on characteristics of optical elements |
| R3 | 47K | 5%, exact value will depend on characteristics of optical elements |
| R7 | 10K | 5% tolerance |
| R8 | 10K | 5% tolerance |
| R9 | 10K | 5% tolerance |
| R10 | 10K | 5% tolerance |
| R11 | 10K | 5% tolerance |
| R12 | 10K | 5% tolerance |
| C1 | 100 nF | Ceramic |
| C2 | 33 pF | Ceramic, exact value to suit crystal used |
| C3 | 33 pF | Ceramic, exact value to suit crystal used |
| Y1 | 4 MHz | Crystal |
| U1 | | PIC16C711-SO20 (XTSO) programmable microcontroller |
| LED1 | | Infrared Emitting Diode |
| Q1 | | Infrared Sensor |
| Display | | Custom 24 segment Triplexed Display |
| SW1 | | Push-to-make contact switch |

Technical Notes on Components

1. LED

Infrared emitting diode e.g. SEP9606.

No special characteristics but to keep current consumption down. A narrow angle high efficiency type preferred.

2. Q1

Infrared Sensor/Photocell e.g. SDP9406

No special characteristics but matched to the wavelength emitted by the LED.

3. Display

The display character height: 6 mm

Temperature range: −5 C. to '40 C.

Connection method to be most economical overall

Digit multiplexed with 3 backplanes

Viewing angle perpendicular to display face

Polarizer to built into display

All segments 'a' will be commoned, all segments 'b' commoned etc.

Those segments that cannot be commoned within the display will be interconnected externally on the PCB.

The rms voltage ratio between a segment being on or off is 1.73.

What is claimed is:

1. A device for measuring air-flow comprising:

a) an air-flow valve including;

at least one rotary blade having a planar surface and carried by a spindle for rotation of the at least one rotary blade about an axis of the spindle to define a path having an outermost part, the planar surface extending radially from the spindle axis to define an outer edge;

a stator including an air deflecting surface and at least one air-directing aperture positioned at or adjacent to the outer edge of said blade or the outermost part of a path traced by the blade during rotation about the spindle axis;

a valve body for housing the stator and the rotary blade and defining an inlet path for air exhaled in a first direction and an annular chamber about the stator; and an air directing means associated with said at least one air directing aperture to guide air from the chamber through the at least one air directing aperture at or towards the planar surface of the at least one rotary blade causing it to rotate about the spindle axis;

whereby air exhaled along the inlet path in the first direction, substantially parallel to the spindle axis, is deflected into the chamber by the air-deflecting surface of the stator, and in the chamber, the air is directed through the at least one air direction aperture and into a second altered direction tangential to the spindle axis and perpendicular to or at least towards the planar surface of said at least one rotary blade;

b) optical elements adapted to transmit and receive an infra-red or light beam through said air-flow valve;

c) electronics for monitoring interruptions to the beam caused by the rotation of the at least one rotary blade about the spindle axis and for determining a required parameter;

d) display means for visually representing the required parameter; and e) a housing for housing the optical elements, electronics and display means;

wherein said air-flow valve is releasably connectable to the housing.

2. A device according to claim 1 further including means for releasably securing said air flow valve in fixed relationship with said housing.

3. A device according to claim 2 wherein said means comprises grooves and positioning flanges on said valve body and securing beads on said housing.

4. A device according to claim 1 wherein said air flow valve is easily assembled and disassembled to facilitate cleaning.

5. A device according to claim 1 wherein said valve is constructed using plastics material components or other suitable materials which withstand regular sterilization.

6. A device according to claim 1 wherein at least part of the valve body, in the region of said blade, is transparent or translucent to allow the passage of said beam through said valve body.

7. A device according to claim 1 wherein apertures are provided in the valve body, in the region of said blade, to allow the passage of said beam therethrough.

8. The device according to claim 1 wherein the air directing means comprise the shape of said at least one air-directing aperture provided in the stator which is profiled to angularly deflect air into a direction tangential to the spindle axis.

9. A device according to claim 1 wherein said air directing means comprises a plurality of fins, each respective fin being positioned on the stator substantially adjacent each of said at least one air-directing aperture.

10. A device according to claim 1 wherein said air directing means comprises a plurality of air-flow guides positioned substantially adjacent each of said at least one air directing aperture.

11. A device according to claim 10 wherein said plurality of air-flow guides are formed as a valve insert adapted to cooperate with the stator, said guides being positioned to correspond to the at least one air directing aperture of the stator.

12. A device according to claim 1 wherein said valve body has an elongate or tubular shape including a mouthpiece which defines the air-inlet path.

13. A device according to claim 12 wherein said mouthpiece is releasably connected to the valve body.

\* \* \* \* \*